United States Patent
Manoury et al.

(10) Patent No.: US 9,149,049 B2
(45) Date of Patent: Oct. 6, 2015

(54) GENETIC CLUSTER OF STRAINS OF STREPTOCOCCUS THERMOPHILUS HAVING UNIQUE RHEOLOGICAL PROPERTIES FOR DAIRY FERMENTATION

(71) Applicant: Dupont Nutrition Bioscienses APS, Copenhagen K (DK)

(72) Inventors: Elise Manoury, Chatellerault (FR); Philippe Horvath, Saint-Gervais-les-3-Clochers (FR); Christophe Fremaux, Poitiers (FR); Pascal Fourcassie, Poitiers (FR)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 0 days.

(21) Appl. No.: 14/289,411

(22) Filed: May 28, 2014

(65) Prior Publication Data

US 2014/0271987 A1    Sep. 18, 2014

Related U.S. Application Data

(63) Continuation of application No. 13/139,148, filed as application No. PCT/EP2009/067099 on Dec. 14, 2009, now Pat. No. 8,771,766.

(60) Provisional application No. 61/121,959, filed on Dec. 12, 2008.

(30) Foreign Application Priority Data

Dec. 12, 2008  (EP) .................................... 08305935

(51) Int. Cl.
| A23C 9/123 | (2006.01) |
| A23C 11/10 | (2006.01) |
| A23C 19/00 | (2006.01) |
| C12R 1/46 | (2006.01) |

(52) U.S. Cl.
CPC ............. *A23C 9/1238* (2013.01); *A23C 11/106* (2013.01); *A23C 19/00* (2013.01); *C12R 1/46* (2013.01); *A23Y 2240/75* (2013.01)

(58) Field of Classification Search
USPC ............................ 426/43, 580, 582, 583, 586
See application file for complete search history.

(56) References Cited

U.S. PATENT DOCUMENTS

| 2008/0124725 A1 | 5/2008 | Barrangou et al. |
| 2010/0034924 A1 | 2/2010 | Fremaux et al. |
| 2011/0002889 A1 | 1/2011 | Barrangou et al. |
| 2012/0149590 A1 | 6/2012 | Klaenhammer et al. |

FOREIGN PATENT DOCUMENTS

| WO | 2004/085607 | 10/2004 |
| WO | 2008/040734 | 4/2008 |

OTHER PUBLICATIONS

Anna et al., J. Rheol., 45(1):115-138 (2001).
Barrangou et al., Science, 315(5819):1709-1712 (2007) XP002428071.
Bolotin et al., Microbiology, 151:2551-2561 (2005).
Corrieu et al., Process, pp. 24-27 (1992).
Database EMBL [Online] Apr. 2, 2007, "Streptococcus therrnophilus strain DGCC7809 CRISPR1 locus genomic sequence." XP002517927.
Database Geneseq [Online] Jan. 24, 2008, "S. thermophilus isolate CRISPR1 nucleotide sequence." XP002517928.
Database Geneseq [Online] Jan. 24, 2008, "S. thermophilus CRISPR1 nucleotide fragment." XP002517929.
Folkenberg et al., International Dairy Journal, 16(2):111-118 (2006) XP005157158.
Horvath et al., J. Bacteriol., 190(4):1401-1412 (2008) XP002517926.
International Search Report and Written Opinion in PCT/EP2009/067099, dated Apr. 23, 2010.
McKinley et al., revised for J. Rheology, pp. 1-28 (2000).
European Search Report in EP 08305935, dated Mar. 6, 2009.

*Primary Examiner* — Michele L Jacobson
*Assistant Examiner* — Bhaskar Mukhopadhyay
(74) *Attorney, Agent, or Firm* — McAndrews, Held & Malloy Ltd.

(57) ABSTRACT

The invention relates to a genetic cluster of strains of *S. thermophilus*, wherein the milk fermented with said strains is highly viscous and weakly ropy. The invention also relates to a genetic cluster of strains of *S. thermophilus*, wherein the genome of said strains comprises a CRISPR locus having the nucleotide sequence of SEQ ID N° 1.

13 Claims, 2 Drawing Sheets

SEQUENCE LISTING

<160> NUMBER OF SEQ ID NOS: 12

<210> SEQ ID NO 1
<211> LENGTH: 895
<212> TYPE: DNA
<213> ORGANISM: Streptococcus thermophilus

<400> SEQUENCE: 1

```
gttttttgtac tctcaagatt taagtaactg tacaactaaa tttattaata tcatcccatc      60
gatctggttt ttgtactctc aagatttaag taactgtaca acggataagg cgagacaaga     120
acaacttaag cagtttttgt actctcaaga tttaagtaac tgtacaacgc gaccatgtaa     180
cgccggtaga aatagcggtt tttgtactct caagatttaa gtaactgtac aaccaaggga     240
gtcgaacccc tgacagccaa caagtttttg tactctcaag atttaagtaa ctgtacaacc     300
gctatgaatg tcgtattaaa agcttttaag tttttgtact ctcaagattt aagtaactgt     360
acaacgactt agggcgctac cccttaaaaa tagcagtttt tgtactctca agatttaagt     420
aactgtacaa ccttatataa aagaaagaca gaaatattct agtttttgta ctctcaagat     480
ttaagtaact gtacaacaac aatggctaag aaattcagcc ctaacgcgtt tttgtactct     540
```

```
caagatttaa gtaactgtac aacacgtttc ctaaatgcat gaaaatcgca aacggttttt    600
gtactctcaa gatttaagta actgtacaac cccctacgaa attttaaaac gaccccccg    660 cgttttgta ctctcaagat ttaagtaact gtacaactac ctacccatgg aacgattact    720
atgcagcgtt tttgtactct caagatttaa gtaactgtac aatgggaagt tataattacg    780
aaaaggtaga tatgtttttg tactctcaag atttaagtaa ctgtacaact atgtcaccac    840
gttgcaaccc tacaccactg tttttgtact ctcaagattt aagtaactgt acaat         895
```

<210> SEQ ID NO 2
<211> LENGTH: 161
<212> TYPE: DNA
<213> ORGANISM: Streptococcus thermophilus

<400> SEQUENCE: 2

```
taaatttatt aatatcatcc catcgatctg gttttgtac tctcaagatt taagtaactg    60
tacaacggat aaggcgagac aagaacaact taagcagttt ttgtactctc aagatttaag    120
taactgtaca acgcgaccat gtaacgccgg tagaaatagc g                        161
```

<210> SEQ ID NO 3
<211> LENGTH: 161
<212> TYPE: DNA
<213> ORGANISM: Streptococcus thermophilus

<400> SEQUENCE: 3

```
ggataaggcg agacaagaac aacttaagca gttttgtac tctcaagatt taagtaactg    60
tacaacgcga ccatgtaacg ccggtagaaa tagcggtttt tgtactctca agatttaagt    120
aactgtacaa ccaagggagt cgaacccctg acagccaaca a                        161
```

<210> SEQ ID NO 4
<211> LENGTH: 161
<212> TYPE: DNA
<213> ORGANISM: Streptococcus thermophilus

<400> SEQUENCE: 4

```
gcgaccatgt aacgccggta gaaatagcgg ttttgtact ctcaagattt aagtaactgt    60
acaaccaagg gagtcgaacc cctgacagcc aacaagtttt tgtactctca agatttaagt    120
aactgtacaa ccgctatgaa tgtcgtatta aaagcttta a                         161
```

<210> SEQ ID NO 5
<211> LENGTH: 162
<212> TYPE: DNA
<213> ORGANISM: Streptococcus thermophilus

<400> SEQUENCE: 5

```
caagggagtc gaacccctga cagccaacaa gttttgtac tctcaagatt taagtaactg    60
tacaaccgct atgaatgtcg tattaaaagc ttttaagttt tgtactctc aagatttaag    120 taactgtaca acgacttagg gcgctacccc ttaaaaatag ca                       162
```

<210> SEQ ID NO 6
<211> LENGTH: 162
<212> TYPE: DNA
<213> ORGANISM: Streptococcus thermophilus

<400> SEQUENCE: 6

```
cgctatgaat gtcgtattaa aagcttttaa gttttgtac tctcaagatt taagtaactg    60
```

```
tacaacgact tagggcgcta ccccttaaaa atagcagttt ttgtactctc aagatttaag    120
taactgtaca accttatata aaagaaagac agaaatattc ta                      162

<210> SEQ ID NO 7
<211> LENGTH: 162
<212> TYPE: DNA
<213> ORGANISM: Streptococcus thermophilus

<400> SEQUENCE: 7
gacttagggc gctacccctt aaaatagca gttttgtac tctcaagatt taagtaactg     60 tacaaccctta tataaagaa agacagaaat attctagttt ttgtactctc aagatttaag  120
taactgtaca acaacaatgg ctaagaaatt cagccctaac gc                     162

<210> SEQ ID NO 8
<211> LENGTH: 163
<212> TYPE: DNA
<213> ORGANISM: Streptococcus thermophilus

<400> SEQUENCE: 8
cttatataaa agaaagacag aaatattcta gttttgtac tctcaagatt taagtaactg   60
tacaacaaca atggctaaga aattcagccc taacgcgttt ttgtactctc aagatttaag  120
taactgtaca acacgtttcc taaatgcatg aaaatcgcaa acg                    163

<210> SEQ ID NO 9
<211> LENGTH: 164
<212> TYPE: DNA
<213> ORGANISM: Streptococcus thermophilus

<400> SEQUENCE: 9
aacaatggct aagaaattca gccctaacgc gtttttgtac tctcaagatt taagtaactg  60
tacaacacgt ttcctaaatg catgaaaatc gcaaacggtt tttgtactct caagatttaa  120
gtaactgtac aaccccctac gaaattttaa acgaccccc ccgc                    164

<210> SEQ ID NO 10
<211> LENGTH: 164
<212> TYPE: DNA
<213> ORGANISM: Streptococcus thermophilus

<400> SEQUENCE: 10
acgtttccta aatgcatgaa aatcgcaaac ggttttgta ctctcaagat taagtaact    60 gtacaacccc ctacgaaatt ttaaaacgac cccccgcgt tttgtactc tcaagattta   120 agtaactgta caactaccta cccatggaac gattactatg cagc                  164

<210> SEQ ID NO 11
<211> LENGTH: 163
<212> TYPE: DNA
<213> ORGANISM: Streptococcus thermophilus

<400> SEQUENCE: 11
cccctacgaa attttaaaac gacccccccg cgttttgta ctctcaagat taagtaact    60 gtacaactac ctacccatgg aacgattact atgcagcgtt tttgtactct caagatttaa  120
gtaactgtac aatgggaagt tataattacg aaaaggtaga tat                    163

<210> SEQ ID NO 12
<211> LENGTH: 162
<212> TYPE: DNA
<213> ORGANISM: Streptococcus thermophilus
```

```
<400> SEQUENCE: 12
tacctaccca tggaacgatt actatgcagc gttttttgtac tctcaagatt taagtaactg         60
tacaatggga agttataatt acgaaaaggt agatatgttt ttgtactctc aagatttaag        120
taactgtaca actatgtcac cacgttgcaa ccctacacca ct                           162
```

GENETIC CLUSTER OF STRAINS OF STREPTOCOCCUS THERMOPHILUS HAVING UNIQUE RHEOLOGICAL PROPERTIES FOR DAIRY FERMENTATION

This application is a continuation of U.S. patent application Ser. No. 13/139,148, filed Jun. 10, 2011 pursuant to 35 U.S.C. 371 as a U.S. National Phase application of International Patent Application No. PCT/EP2009/067099, which was filed Dec. 14, 2009, claiming the benefit of priority to European Patent Application No. 08305935.2, which was filed on Dec. 12, 2008, and U.S. Provisional Patent Application No. 61/121,959, which was filed on Dec. 12, 2008. The text of the aforementioned applications is incorporated herein by reference in its entirety.

FIELD OF THE INVENTION

The invention relates to a genetic cluster of strains of *Streptococcus thermophilus* (*S. thermophilus*) having unique rheological properties for dairy fermentation.

BACKGROUND OF THE INVENTION

*S. thermophilus* strains are used extensively alone or in combination with other *S. thermophilus* strains or in combination with other microorganisms for the production of fermented food products. For instance, they are included in the formulation of the starter cultures used for yogurt production. Strains of *S. thermophilus* are expected to participate in the formation of lactic curd by acidification of milk and in the development of the texture of the fermented product. *S. thermophilus* strains are thus generally characterized by their functional properties, i.e. their acidifying and texturizing properties. A texturizing strain is a strain enabling to obtain fermented milks which can be described by their rheological properties, such as viscosity and ropiness. The texturizing *S. thermophilus* strains known to date can be classified in three groups based on these rheological properties: 1) high viscosity and high ropiness, 2) low viscosity and low ropiness and 3) average viscosity and ropiness. However, it would be interesting to have a strain of *S. thermophilus* having rheological properties enabling to obtain fermented milks having a high viscosity and a low ropiness.

Thus one of the problems the invention proposes to resolve is to provide novel strains of *S. thermophilus* which produce fermented milks having a high viscosity and a low ropiness.

SUMMARY OF THE INVENTION

During their research, the inventors have found a new genetic cluster of strains of *S. thermophilus* having unique rheological properties for dairy fermentation: the milk fermented with the strains of the invention is highly viscous and weakly ropy. The inventors also discovered that, in addition to these unique rheological properties, the genome of these strains surprisingly comprises a CRISPR locus having the sequence of SEQ ID N°1 which was unknown to date.

CRISPR (Clustered Regularly Interspaced Short Palindromic Repeats) are highly polymorphic loci which are known to confer resistance to phages (Barrangou et al., Science. 2007 Mar. 23; 315(5819):1709-12; Horvath et al., J Bacteriol. 2008 February; 190(4):1401-12; Deveau et al., J Bacteriol. 2008 February; 190(4):1390-400). CRISPR loci are composed of short, conserved DNA repeats that are separated by unique sequences of similar size named spacers. It is the spacer content, in terms of spacer nucleotide sequence and spacer arrangement, that is specific to any given family of strains (Horvath et al., J Bacteriol. 2008 February; 190(4):1401-12). In the *S. thermophilus* genome, up to three CRISPR loci can be present simultaneously, depending on the strain. It has been suggested that the CRISPR loci are the most rapidly evolving regions in the *S. thermophilus* genome, and thus are very relevant targets to consider for strain differentiation and identification (Bolotin et al. Microbiology. 2005 August; 151 (Pt 8):2551-61; Horvath et al. J Bacteriol. 2008 February; 190(4):1401-12).

Accordingly, thanks to this new CRISPR sequence, the strains of *S. thermophilus* of the invention can be easily identified: *S. thermophilus* strains having the same CRISPR sequence in their genome can be identified as members of the same family of strains, thus sharing the same technical properties, i.e. the unique rheological properties as described previously.

The invention thus relates, in a first aspect, to strains of *S. thermophilus*, wherein the milk fermented with said strains has a viscosity greater than about 55 Pa·s when measured with Test A and a Caber Relative Break-up Time of less than about 0.015 second when measured with Test B.

The invention also relates, in another aspect, to a genetic cluster of strains of *S. thermophilus*, wherein the genome of said strains comprises a CRISPR locus having the nucleotide sequence of SEQ ID N°1.

The invention still relates to a genetic cluster of strains of *S. thermophilus*, wherein the genome of said strains comprises a CRISPR locus comprising a nucleotide sequence selected from the group consisting of SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 and SEQ ID N°12.

Another object of the invention is the strain of *S. thermophilus* deposited under the Budapest Treaty on 7th of Oct. 2008 in the name of Danisco Deutschland GmbH at the Deutsche Sammlung von Mikroorganismen and Zellkulturen under number DSM 21892.

The invention also relates to a bacterial composition comprising a strain according to the invention.

Still another object of the invention is a method for preparing fermented dairy products, wherein said method comprises fermenting a milk substrate with a *S. thermophilus* strain according to the invention or with the bacterial composition as defined previously.

The invention also relates to a dairy product obtainable by the method as defined previously.

The invention still relates to the use of a strain according to the invention or of the bacterial composition according to the invention for preparing fermented dairy products.

A subject of the invention is also a dairy product comprising a strain according to the invention or the bacterial composition as defined previously.

DETAILED DESCRIPTION OF THE INVENTION

The invention relates, in a first aspect, to strains of *S. thermophilus*, wherein the milk fermented with said strains is highly viscous and weakly ropy. Typically, the milk fermented with a strain of the invention has a viscosity greater than about 55 Pa·s when measured with Test A and a Caber Relative Break-up Time of less than about 0.015 second when measured with Test B.

Typically, the previously mentioned viscosity of the milk fermented with a strain according to the invention is greater than about 56, 57, 58, 59, 60 or 61 Pa·s. In addition, said viscosity is typically lower than 80 Pa·s. In particular, the viscosity is lower than 75, 70 or 65 Pa·s.

Still typically, the above mentioned milk fermented with a strain of the invention has a Caber Relative Break-up Time of 0 to 0.015 second when measured with Test B. In particular said Caber Relative Break-up Time is lower than about 0.014, 0.013, 0.012, 0.011 or 0.010 second.

Within the scope of the invention, it is encompassed any combination of the above viscosity and Caber Relative Break-up Time values.

According to the invention, the viscosity of the milk fermented with the strain of the invention is measured by Test A. This test is fully described in the experimental section. Briefly, measuring the viscosity according to Test A comprises the following steps:

1) obtaining a milk fermented with a strain of *S. thermophilus* by:
   heating at 90° C. for 10 min commercial half-fat UHT milk (fat 1.5% w/w) completed with 3% skimmed milk powder,
   adding 1 g/100 L (w/v) of sodium formiate just before inoculation,
   inoculating the milk with $1.10^6$ cfu/ml of milk of a strain of *S. thermophilus* preserved at −80° C. in milk based medium,
   incubating the inoculated milk at a constant temperature of 43° C.+/−1° C. in a water bath until the pH reaches 4.60+/−0.1, the pH being measured with a Cinac system,
   cooling down the fermented milk to 6° C., and then storing the fermented milk at 6° C. for 14 days, 2) measuring, at a temperature of 8° C.+/−2° C., the viscosity of the fermented milk obtained according to step 1) by:
   mounting a Brookfield viscometer (Brookfield Engineering laboratories, Inc.) on helipath stand,
   equipping said viscometer with a T-bar spindle type C,
   filling a 125 mL glass yogurt pot with the fermented milk,
   introducing the yogurt pot filled with the fermented milk in the viscometer,
   applying a speed of 10 rpm to the viscometer, and then reading, after 30 seconds of rotation, the viscosity of the sample.

A Cinac system according to the invention is for instance described in the following reference: CINAC, an automated system for control of lactic starters; Corrieu-G, Picque-D, Perret-B, Quemener-P; Process Magazine; 1992; no. 1068; p. 24-27.

Within the meaning of the invention, the Relative Break-up Time is the time needed for a fluid filament to go, at a temperature of 20° C., from a diameter of 55 μm until its breaks with a standard deviation of +/−8% when measured with a Capillary Break-up Extensional Rheometer. According to the invention, the Caber Relative Break-up Time of the fermented milk is measured by Test B. This test is fully described in the experimental section. Briefly, measuring the viscosity according to Test B comprises the following steps:

1) obtaining a fermented milk with a strain of *S. thermophilus* as described in step 1) of Test A, 2) measuring the Caber Relative Break-up Time of the milk fermented with the strain of *S. thermophilus* by:
   warming a sample of the fermented milk obtained at step 1) to 20° C.,
   breaking and homogenizing the gel by stirring 20 times with a standard plastic spoon,
   placing 60 μL of the homogenized fermented milk between two plates of a Capillary Break-up Extensional Rheometer (CaBER 1 from HAAKE, THERMO ELECTRON Corp.) having the following settings:
   plate diameter: 6 mm
   initial height: 2 mm
   final height: 9.65 mm
   strike speed: 0.24 mm/ms (Strike time: 40 ms)
   laser-micrometer: class 1 laser operating in the infrared and having a resolution of 10 μm,
   and then
   measuring the Relative Break-up Time of the sample.

The invention also relates, in another aspect, to a genetic cluster of strains of *S. thermophilus*, wherein the genome of said strains comprises a CRISPR locus having the nucleotide sequence of SEQ ID N°1.

The sequence SEQ ID N°1 of the CRISPR locus (leader to trailer orientation, Horvath et al., J Bacteriol. 2008 February; 190(4):1401-12) of the strains of *S. thermophilus* of the invention is shown below, with the repeats in uppercase letters and the spacers in lowercase letters:

```
5'-GTTTTTGTACTCTCAAGATTTAAGTAACTGTACAACtaaatttattaatatcatcccatcgatctg

GTTTTTGTACTCTCAAGATTTAAGTAACTGTACAACggataaggcgagacaagaacaacttaagca

GTTTTTGTACTCTCAAGATTTAAGTAACTGTACAACgcgaccatgtaacgccggtagaaatagcg

GTTTTTGTACTCTCAAGATTTAAGTAACTGTACAACcaagggagtcgaaccctgacagccaacaa

GTTTTTGTACTCTCAAGATTTAAGTAACTGTACAACcgctatgaatgtcgtattaaaagcttttaa

GTTTTTGTACTCTCAAGATTTAAGTAACTGTACAACgacttagggcgctaccccttaaaaatagca

GTTTTTGTACTCTCAAGATTTAAGTAACTGTACAACcttatataaaagaaagacagaaatattcta

GTTTTTGTACTCTCAAGATTTAAGTAACTGTACAACaacaatggctaagaaattcagccctaacgc

GTTTTTGTACTCTCAAGATTTAAGTAACTGTACAACacgthcctaaatgcatgaaaatcgcaaacg

GTTTTTGTACTCTCAAGATTTAAGTAACTGTACAACccctacgaaatttaaaacgacccccccgc

GTTTTTGTACTCTCAAGATTTAAGTAACTGTACAACtacctacccatggaacgattactatgcagc

GTTTTTGTACTCTCAAGATTTAAGTAACTGTACAATgggaagttataattacgaaaaggtagatat
```

```
GTTTTTGTACTCTCAAGATTTAAGTAACTGTACAACtatgtcaccacgttgcaaccctacaccact

GTTTTTGTACTCTCAAGATTTAAGTAACTGTACAAT-3'
```

SEQ ID N°1 contains 14 repeats that are nearly identical; only the twelfth and fourteenth repeats have one different base at their 3' end (T instead of C). These repeats define 13 spacers, all unique and different from the 971 non redundant S. thermophilus CRISPR spacer sequences that are present in GenBank (accession numbers CP000023, CP000024, CP000419, DQ072985 to DQ073008, and EF434458 to EF434504) or described in Horvath et al. (J Bacteriol. 2008 February; 190(4):1401-12). This observation indicates that the strains of S. thermophilus of the invention possess unique genetic features that can be exploited to unambiguously identify and track these technologically unique strains.

The invention also pertains to a genetic cluster of strains of S. thermophilus, wherein the genome of said strains comprises a CRISPR locus having the nucleotide sequence of a derivative of SEQ ID N°1.

According to the invention, a derivative of SEQ ID N°1 is a nucleotide sequence having at least 90% of identity with SEQ ID N°1, particularly at least 95% of identity with SEQ ID N°1, more particularly at least 98% of identity with SEQ ID N°1 and most particularly at least 99% of identity with SEQ ID N°1.

To determine the percent identity of two nucleic acid sequences, the sequences are aligned for optimal comparison. For example, gaps can be introduced in the sequence of a first nucleic acid sequence for optimal alignment with the second nucleic acid sequence. The nucleotides at corresponding nucleotide positions are then compared. When a position in the first sequence is occupied by the same nucleotide as at the corresponding position in the second sequence, the nucleic acids are identical at that position. The percent identity between the two sequences is a function of the number of identical nucleotides shared by the sequences.

Hence % identity=[number of identical nucleotides/total number of overlapping positions]×100. The percentage of sequence identity is thus calculated according to this formula, by comparing two optimally aligned sequences over the window of comparison, determining the number of positions at which the identical nucleic acid base (e. g., A, T, C, G) occurs in both sequences to yield the number of matched positions (the "number of identical positions" in the formula above), dividing the number of matched positions by the total number of positions in the window of comparison (e. g. the window size) (the "total number of overlapping positions" in the formula above), and multiplying the result by 100 to yield the percentage of sequence identity.

In this comparison, the sequences can be the same length or may be different in length. Optimal alignment of sequences for determining a comparison window may be conducted by the local homology algorithm of Smith and Waterman (1981), by the homology alignment algorithm of Needleman and Wunsh (1972), by the search for similarity via the method of Pearson and Lipman (1988), by computerized implementations of these algorithms (GAP, BESTFIT, FASTA and TFASTA in the Wisconsin Genetics Software Package Release 7.0, Genetic Computer Group, 575, Science Drive, Madison, Wis.), or by inspection.

Typically, a derivative having at least 90% of identity with SEQ ID NO:1 comprises for example an average number of 3 mutations per spacer and repeat, i.e. 81 mutations. It will be easily understood by the skilled person that an "average number of 3 mutations per spacer and repeat" means that one or more repeats or spacers may comprise more than 3 mutations, e.g. 4, 5, 6, 7 or more, whereas other spacers or repeats may comprise less than 3 mutations, e.g. 2, 1 or 0 mutations.

The percent identity is thus calculated as follows:
number of identical positions: 895−81=814
total number of overlapping positions: 895
percent identity: (814/895)*100=90.9%.

Typically, a derivative having at least 95% of identity with SEQ ID NO:1 comprises for example an average number of 3 mutations per spacer, i.e. 39 mutations. It will be easily understood by the skilled person that an "average number of 3 mutations per spacer" means that one or more spacers may comprise more than 3 mutations, e.g. 4, 5, 6, 7 or more, whereas other spacers may comprise less than 3 mutations, e.g. 2, 1 or 0 mutations.

The percent identity is thus calculated as follows:
number of identical positions: 895−39=856
total number of overlapping positions: 895
percent identity: (856/895)*100=95.6%.

Typically, a derivative having at least 98% of identity with SEQ ID NO:1 comprises for example an average number of 1 mutation per spacer, i.e. 13 mutations. It will be easily understood by the skilled person that an "average number of 1 mutation per spacer" means that one or more spacers may comprise more than 1 mutation, e.g. 2, 3, 4, 5, 6, 7 or more, whereas other spacers may not comprise any mutation.

The percent identity is thus calculated as follows:
number of identical positions: 895−13=882
total number of overlapping positions: 895
percent identity: (882/895)*100=98.5%.

Typically, a derivative having at least 99% of identity with SEQ ID NO:1 comprises for example one mutation in its sequence, particularly in a spacer. The percent identity is thus calculated as follows:
number of identical positions: 895−1=894
total number of overlapping positions: 895
percent identity: (894/895)*100=99.8%.

As used herein, "mutation" means deletion, substitution or insertion of a nucleotide of a nucleotide sequence.

Accordingly, a strain of S. thermophilus, the genome of which comprises a CRISPR sequence corresponding to a derivative sequence of SEQ ID N°1 as defined previously, will have the rheological properties according to the invention.

In addition, since the 13 spacers of SEQ ID N°1 are all unique and different from the other S. thermophilus CRISPR spacer sequences know to date, the detection of at least three above mentioned successive spacers separated by the above mentioned repeats in the genome of a S. thermophilus strain is sufficient to identify a strain of S. thermophilus according to the invention, i.e. having the previously mentioned rheological properties. The detection of at least three spacers/repeats is not arbitrary. Indeed, the current understanding about the way CRISPR sequences evolve indicates that the probability of having a strain of S. thermophilus (unrelated to the strain according to the invention) containing one of these spacers is significant; two of these consecutive spacers is rare, and three of these consecutive spacers is very low.

The invention thus also relates to a genetic cluster of strains of S. thermophilus, wherein the genome of said strains comprises a CRISPR locus comprising a nucleotide sequence selected from the group consisting of SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 and SEQ ID N°12.

These sequences, SEQ ID N°2 to 12, correspond to 3 consecutive spacers separated by 2 repeats of the CRISPR locus.

The invention also pertains to a genetic cluster of strains of *S. thermophilus*, wherein the genome of said strains comprises a CRISPR locus comprising a derivative of a nucleotide sequence selected from the group consisting of SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 and SEQ ID N°12.

According to the invention, a derivative of SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 or SEQ ID N°12 is a nucleotide sequence having at least 90% of identity, particularly at least 94% of identity, more particularly at least 96% of identity, most particularly at least 99% of identity with SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 or SEQ ID N°12 respectively.

The percent identity is calculated as described previously.

Typically, a derivative having at least 90% of identity with one of SEQ ID NO:2 to SEQ ID NO:12 comprises for example an average number of 3 mutations per spacer and repeat, i.e. 15 mutations. It will be easily understood by the skilled person that an "average number of 3 mutations per spacer and repeat" means that one or more repeats or spacers may comprise more than 3 mutations, e.g. 4, 5, 6, 7 or more, whereas other spacers or repeats may comprise less than 3 mutations, e.g. 2, 1 or 0 mutations.

The percent identity is thus calculated as follows:
number of identical positions: 163−15=148
total number of overlapping positions: 163
percent identity: (148/163)*100=90.8%.

Typically, a derivative having at least 94% of identity with one of SEQ ID NO:2 to SEQ ID NO:12 comprises for example an average number of 3 mutations per spacer, i.e. 9 mutations. It will be easily understood by the skilled person that an "average number of 3 mutations per spacer" means that one or more spacers may comprise more than 3 mutations, e.g. 4, 5, 6, 7 or more, whereas other spacers may comprise less than 3 mutations, e.g. 2, 1 or 0 mutations.

The percent identity is thus calculated as follows:
number of identical positions: 163−9=154
total number of overlapping positions: 163
percent identity: (154/163)*100=94.4%.

Typically, a derivative having at least 96% of identity with one of SEQ ID NO:2 to SEQ ID NO:12 comprises for example an average number of 1 mutation per spacer and repeat, i.e. 5 mutations. It will be easily understood by the skilled person that an "average number of 1 mutation per spacer and repeat" means that one or more repeats or spacers may comprise more than 1 mutations, e.g. 2, 3, 4, 5, whereas other spacers or repeats may not comprise any mutation.

The percent identity is thus calculated as follows:
number of identical positions: 163−5=158
total number of overlapping positions: 163
percent identity: (158/163)*100=96.9%.

Typically, a derivative having at least 99% of identity with one of SEQ ID NO:2 to SEQ ID NO:12 comprises for example one mutation in its sequence, particularly in a spacer.

The percent identity is thus calculated as follows:
number of identical positions: 163−1=162
total number of overlapping positions: 163
percent identity: (162/163)*100=99.3%.

Accordingly, a strain of *S. thermophilus*, the genome of which comprises a CRISPR sequence corresponding to a derivative sequence of anyone of SEQ ID N°2 to 12 as defined previously, will have the rheological properties according to the invention.

The presence of SEQ ID N°1 to SEQ ID N°12 or a derivative thereof in the genome of *S. thermophilus* strains can be easily detected by any known method by the skilled person.

For instance, the skilled person can easily perform a PCR with primers selected in the spacers' sequences, or DNA-DNA hybridization with probes corresponding to the spacers, or sequencing one or several CRISPR loci in the genome of the strain.

Therefore, the invention also relates to a method for predicting a strain's membership of a family of strains the genome of which comprises the nucleotide sequence of SEQ ID N°1 to SEQ ID N°12 or a derivative thereof.

Typically, the strains belonging to the above defined genetic cluster of strains of *S. thermophilus* have unique rheological properties. Within the meaning of the invention, by unique rheological properties, it is meant a strain which produces fermented milk having a viscosity greater than about 55 Pa·s when measured with Test A and a Caber Relative Break-up Time of less than about 0.015 second when measured with Test B; Tests A and B being as defined previously.

Typically, a strain according to the invention is the strain of *S. thermophilus* deposited under the Budapest Treaty on 7$^{th}$ of Oct. 2008 in the name of Danisco Deutschland GmbH at the Deutsche Sammlung von Mikroorganismen und Zellkulturen, located Inhoffenstr. 7 B, D-38124 Braunscheiwg, Germany, under number DSM 21892 or a mutant thereof which retains the same rheological properties.

In order to obtain such mutant strains, a person skilled in the art can use the usual mutagenesis techniques such as UV irradiation or exposure to mutagenic chemical products (ethyl-methane-sulfonate, N-methyl-N'-nitro-N-nitrosoguanidine, nitrous acid, nucleotide base analogues such as bromouracil, and acridines etc.), but it is contemplated that any other effective mutagen will be suitable.

In one embodiment, the mutant strains are phage insensitive. The spectrum of a strain's sensitivity to the bacteriophages, also called lysotype, is constituted by all of the sensitivities and resistances to said bacteriophages. For instance, a method for determining the lysotype of a strain of *S. thermophilus* and therefore its sensitivity to phage infection is fully described in WO2008040734. In accordance with conventional mutagenesis techniques, the mutagenesis is followed by suitable selection of the strains which have the unique rheological properties of the strains of the invention, which can be measured by Tests A and B as defined above.

A particular object of the invention is the strain of *S. thermophilus* deposited under the Budapest Treaty on 7$^{th}$ of Oct. 2008 in the name of Danisco Deutschland GmbH at the Deutsche Sammlung von Mikroorganismen und Zellkulturen under number DSM 21892.

The invention also relates to a bacterial composition comprising a strain according to the invention. By bacterial composition is meant a mixture of different strains, in particular a starter culture, or a leaven.

The mixtures of preferred strains according to the invention are mixtures of *S. thermophilus* with other *S. thermophilus*, or mixtures of *S. thermophilus* with *Lactobacillus del-*

*brueckii* subsp. *bulgaricus*, or mixtures of *S. thermophilus* with other *Lactobacillus* and/or with *Bifidobacterium*, or mixtures of *S. thermophilus* with *Lactococcus*, or mixtures of *S. thermophilus* with other strains of lactic bacteria and/or yeasts.

Another object of the invention is a method for preparing fermented dairy products, wherein said method comprises fermenting a milk substrate with a *S. thermophilus* strain according to the invention or with the bacterial composition as defined previously.

Typically, the milk substrate is natural or reconstituted milk, skimmed or otherwise, or milk-based media or media based on products of dairy origin. This milk substrate may comprise items commonly used for the preparation of milk desserts. Typically said items commonly used for the preparation of milk desserts are solid items such as for example fruits, chocolate chips or cereals, but also sweetened products or liquid chocolates.

The invention also relates to a dairy product obtainable by the method as defined previously.

The invention still relates to the use of a strain according to the invention or of the bacterial composition according to the invention for preparing fermented dairy products.

A subject of the invention is also a dairy product comprising a strain according to the invention or the bacterial composition as defined previously.

Within the meaning of the invention, by "dairy product" is meant fermented milk, a yogurt, a matured cream, a cheese, a fromage frais, a milk drink, a dairy product retentate, a processed cheese, a cream dessert, a cottage cheese or an infant milk. Still typically, the dairy product according to the invention comprises milk of animal and/or plant origin.

The present invention is better illustrated below using the examples which follow. These examples are given only by way of illustration of the subject-matter of the invention, of which they in no way constitute a limitation.

EXAMPLE

Ropiness and Viscosity Evaluation of Fresh Fermented Milks

Preparation of Fresh Fermented Milks

Fermented milks have been prepared according to the following experimental conditions:

Preparation of Milk-Base:

Commercial half-fat UHT milk (fat 1.5% w/w)+3% skimmed milk powder was heat treated at 90° C. for 10 min. Just before inoculation. 1 g/100 L (w/v) of sodium formiate was added.

Inoculation:

The inoculation was performed with strain preserved at −80° C. in milk based medium. The inoculation rate was $1.10^6$ cfu/ml of milk-base.

Fermentation:

The incubation temperature is set at 43° C.+/−1° C., and kept constant in a water bath during the fermentation. A Cinac system (CINAC, an automated system for control of lactic starters; Corrieu-G, Picque-D, Perret-B, Quemener-P; Process Magazine; 1992; no. 1068; p. 24-27) is used for on-line measurement of pH change. At pH 4.60+/−0.1, the fermented product is cooled down to 6° C. then stored at 6° C. for 14 days.

For the evaluation of ropiness, two different techniques had been performed. The first one is based on extensional rheology measurement and the second one is based on sensory assessment.

Description and Principle of the Extensional Rheometer CaBER 1 to Assess Extensional Properties of Fresh Fermented Milks The concept of extensional rheometry is analogous to shear rheometry. But instead of obtaining the shear viscosity by applying a known force in shear and measuring the resulting displacement, a similar procedure is carried out in extension. The force is applied uni-directionally. This principle allows the measurement of the elasticity component of the texture of a given product.

The Capillary Break-up Extensional Rheometer (CaBER 1 apparatus from HAAKE, THERMO ELECTRON Corporation) is an apparatus designed to assess the extensional viscosity of a product. It has been developed by the Cambridge Polymer Group (G. H. Mckinley et al. J. Rheo. 2000 44(3): 653-70; S. L. Anna et al. J. Rheo. 2001 45(1): 115-38).

To measure the extensional viscosity, 60 ml of fresh fermented milk are placed between 2 parallel circular plates. The product is submitted to a rapid extension by moving the upper plate upwards, forming a fluid filament. Then, a laser micrometer measures the diameter of the thinning filament.

The midpoint diameter of the gradually thinning fluid filament starts being measured after the upper plate has reached its final position. The apparatus records the thinning of the fluid filament (1000 measurements per second). The evolution of the diameter of the filament over time can be plotted. This allows the determination of the initial diameter of the filament and of its break-up time.

A specific protocol was developed by the inventors to assess the break-up time value for fresh fermented milks. The fresh fermented milk is prepared as described above. The sample is warmed to 20° C. The gel is broken and homogenized by stirring (20 stirs) using a standard plastic spoon. An aliquot of the sample is taken using a Multipette Plus (Eppendorf) and 0.5 ml combitips (Eppendorf). 60 µl are placed between the 2 plates of the CaBER. The following setting of the CaBER was used:

Plate diameter: 6 mm
Initial Height: 2 mm
Final Height: 9.65 mm
Strike Speed: 0.24 mm/ms (Strike Time: 40 ms)

For each sample, 4 measurements are done. The data used to qualify the extensional viscosity of the sample is the Relative Break-up Time (RBT). RBT is the time needed for a fluid filament to go from a diameter of 55 µm until it breaks. The standard deviation of the method has been calculated to be +/−8%.

Assessment of Ropiness by Sensory Tasting

Training on the "Ropy" Descriptor

The sensory tasting sessions involve 3 specialist assessors. These assessors are asked to evaluate the products in blind conditions (the fermented milks are coded) on a specific texture descriptor: "ropy". "Ropy" is evaluated as follows: with a spoonful of fermented milk tilted a few centimeters above the cup, the ability of the product to run continuously and to form an unbroken rope is evaluated.

The fermented milks are ranked from rank 0 for a "non-ropy" fermented milk (no rope) to rank 4 for very "ropy"

fermented milk (long unbroken rope). Then, a consensus rank is agreed by the 3 assessors. This consensual rank is reported.

In order to train the specialist assessors in the evaluation of the "ropy" descriptor, 3 fermented milks were prepared using 3 reference strains:

Rank 0: ropiness of a fermented milk made with strain CNCM I-2429

Rank 2: ropiness of a fermented milk made with strain CNCM I-2423

Rank 4: ropiness of a fermented milk made with strain CNCM I-2980

Testing of Fresh Fermented Milks

Six fresh fermented milks were produced according to the protocol described previously. Fresh fermented milks were obtained by inoculation with six single strains, respectively: DSM 21892, CNCM I-3617, DSM 18344, CNCM I-2429, CNCM I-2423 and CNCM I-2980.

The strains CNCM I-2429, CNCM I-2423, CNCM I-2980 and CNCM I-3617 were mentioned for example in the published patent application WO08/040734 filed by Danisco A/S on the Feb. 10, 2007. The strain DSM 18344 was mentioned for example in WO07/144770 filed by Danisco A/S on the Aug. 6, 2007.

The fermented milk obtained with CNCM I-2429 was assessed rank 0 for ropiness, as expected. Similarly, fermented milks obtained with CNCM I-2423 and CNCM I-2980 were assessed rank 2 and rank 4 (see FIG. 1), respectively; thus validating the data obtained for the other fermented milks. The fermented milk made with DSM 21892 got a consensual rank of 0 for ropy evaluation. Consensual rank for the ropy evaluation was 1 and 3 for the fermented milks made with CNCM I-3617 and DSM 18344, respectively (see FIG. 1).

Sensory Ropiness Level is Related to RBT Value

Figure 1:
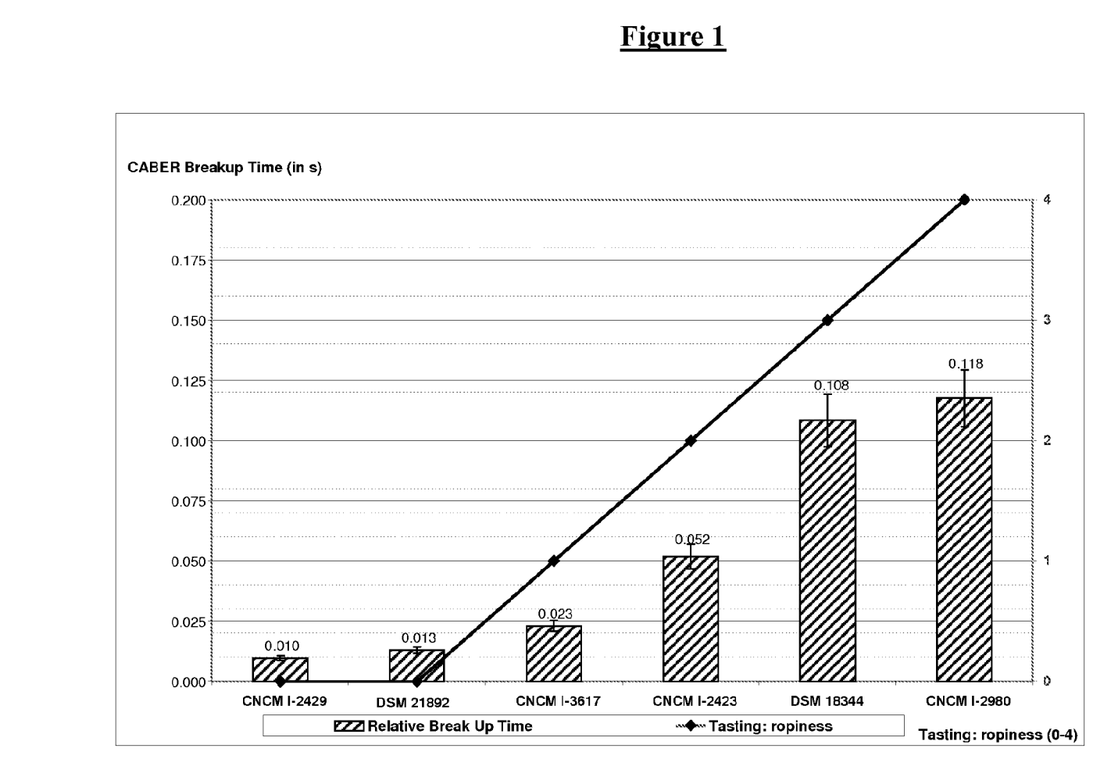
FIG. 1: Relation between sensory attribute "ropy" level and Relative Break-up Time (RBT) measured with the CaBER 1 in six fermented milks.

The RBT values were also measured with the CaBER1 for the six fermented milks tested. Globally, increases in sensory ropiness correlate increases in Caber Relative Break-up Time (FIG. 1). This result points out that the two parameters are quite linked. The fermented milk made with DSM 21892 has a low value for Relative break-up Time, as the fermented milk made with the strain CNCM I-2429 (i.e. <0.015 s). The reference very ropy strain CNCM I-2980 has a high level for this parameter (0.118 s).

Milk Fermented with Strain DSM 21892 Present Unique Rheological Characteristics Which can be Qualified as Highly Thick and Weakly Ropy.

A Brookfield viscometer (Brookfield Engineering laboratories, Inc.) was used to rate viscosity. The apparatus was mounted on helipath stand (Brookfield Engineering laboratories. Inc.). The viscometer is equipped with a T-bar spindle type C and the speed applied is 10 rpm. The viscosity is measured at a temperature of 8° C.+/−2° C. and is read after 30 s of rotation. It is generally recognised that viscosity level is directly linked to thickness attribute level evaluated by sensory tasting session (see patent WO 2004/085607 A2).

Figure 2:
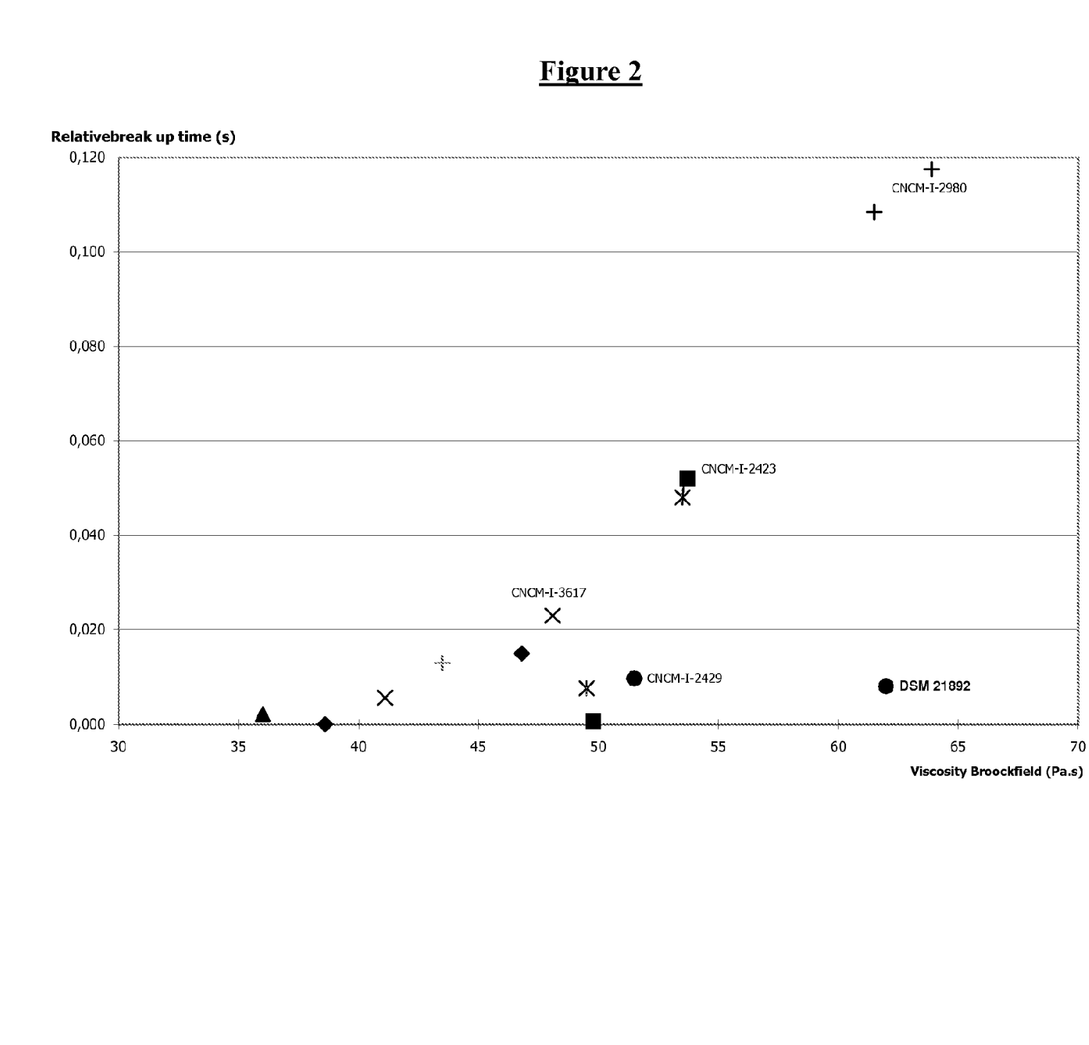
FIG. 2: Rheological characteristics, viscosity and Relative Break up time, of 14 milks fermented with 14 different strains of *S. thermophilus* strains.

The FIG. 2 reports the relative positioning of 14 fresh fermented milks, produced with 14 different strains of *S. thermophilus*, for viscosity and Relative break-up time response (RBT).

The strains CNCM I-2429, CNCM I-2423, CNCM I-2980, CNCM I-3617 were mentioned for example in the published patent application WO08/040734 filed by Danisco A/S on the Feb. 10, 2007.

As a general trend, viscosity of the fresh fermented milk increases linearly with the RBT value, except for the strain DSM 21892 which keeps a low RBT value although viscosity becomes significantly high, more than 55 Pa·s.

CONCLUSION

The combination of these unique rheological properties, i.e. low ropiness and high viscosity, which was never contemplated to date, confers to the strains according to the invention very promising applications, in particular for the development of new dairy products having unique and new textures never proposed yet.

REFERENCES

Throughout this application, various references describe the state of the art to which this invention pertains. The disclosures of these references are hereby incorporated by reference into the present disclosure.

The invention claimed is:

1. A method for preparing fermented dairy products, wherein said method comprises fermenting a milk substrate with a strain of *Streptococcus thermophilus*, wherein the genome of said strain comprises a CRISPR locus comprising a nucleotide sequence selected from the group consisting of SEQ ID N°1, SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11, and SEQ ID N°12 and a derivative nucleotide sequence having at least 90% identity with SEQ ID N°1, SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 or SEQ ID N°12 and wherein when said strain ferments milk, the fermented milk has a viscosity greater than about 55 Pa·s and lower than about 80 Pa·s. when measured with Test A and a Caber Relative Break-up Time of less than about 0.015 seconds when measured with Test B.

2. The method according to claim 1, wherein the genome of said strain comprises a CRISPR locus having the nucleotide sequence of SEQ ID N°1, or a derivative thereof having at least 90% identity with SEQ ID N°1.

3. The method according to claim 1, wherein said derivative nucleotide sequence has at least 95% of identity with SEQ ID N°1.

4. The method according to claim 1, wherein said derivative nucleotide sequence has at least 94% of identity with SEQ ID N°2, SEQ ID N°3, SEQ ID N°4, SEQ ID N°5, SEQ ID N°6, SEQ ID N°7, SEQ ID N°8, SEQ ID N°9, SEQ ID N°10, SEQ ID N°11 or SEQ ID N°12.

5. The method according to claim 1, wherein said strain is the strain of *Streptococcus thermophilus* deposited under the Budapest Treaty on 7th of October 2008 in the name of Danisco Deutschland GmbH at the Deutsche Sammlung von Mikroorganismen and Zellkulturen under number DSM 21892 or a mutant thereof.

6. The method according to claim 1, wherein when said strain ferments milk, the fermented milk has a viscosity greater than about 56, 57, 58, 59, 60 or 61 Pa·s when measured with Test A.

7. The method according to claim 1, wherein when said strain ferments milk, the fermented milk has a Caber Relative Break-up Time of less than about 0.014, 0.013, 0.012, 0.011 or 0.010 second when measured with Test B.

8. The method according to claim 1, wherein said method comprises fermenting a milk substrate with a mixture of different strains including said strain of *Streptococcus thermophilus*.

9. The method according to claim 8, wherein said mixture is a mixture of different *S. thermophilus* strains, or a mixture of *S. thermophilus* with *Lactobacillus delbrueckii* subsp. *bulgaricus*, or a mixture of *S. thermophilus* with other *Lactobacillus* and/or with *Bifidobacterium*, or a mixture of *S. thermophilus* with *Lactococcus*, or a mixture of *S. thermophilus* with other strains of lactic bacteria and/or yeasts.

10. The method according to claim 1, wherein the milk substrate is natural or reconstituted milk, skimmed or otherwise, or milk-based media or media based on products of dairy origin.

11. The method according to claim 1, wherein the milk substrate comprises items commonly used for the preparation of milk desserts, selected from the group consisting of fruits, chocolate chips, cereals, sweetened products and liquid chocolates.

12. The method according to claim 1, wherein said dairy product is a fermented milk, a yogurt, a matured cream, a cheese, a fromage frais, a milk drink, a dairy product retentate, a processed cheese, a cream dessert, a cottage cheese or an infant milk.

13. The method according to claim 1, wherein said dairy product comprises milk of animal and/or plant origin.

* * * * *